United States Patent
Kim et al.

(10) Patent No.: US 10,353,114 B2
(45) Date of Patent: Jul. 16, 2019

(54) DUAL CAP FOR PROTECTING HUMIDITY SENSOR OF RADIOSONDE

(71) Applicant: Korea Research Institute of Standards and Science, Daejeon (KR)

(72) Inventors: Yong-Gyoo Kim, Daejeon (KR); Byung Il Choi, Daejeon (KR); Sang Wook Lee, Chungcheongnam-do (KR); Jong Cheol Kim, Daejeon (KR); Sang Bong Woo, Daejeon (KR); Dae Ho Kim, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 217 days.

(21) Appl. No.: 15/120,040

(22) PCT Filed: May 21, 2015

(86) PCT No.: PCT/KR2015/005084
§ 371 (c)(1),
(2) Date: Aug. 18, 2016

(87) PCT Pub. No.: WO2016/010251
PCT Pub. Date: Jan. 21, 2016

(65) Prior Publication Data
US 2017/0059745 A1 Mar. 2, 2017

(30) Foreign Application Priority Data
Jul. 18, 2014 (KR) .................. 10-2014-0090972

(51) Int. Cl.
*G01W 1/08* (2006.01)
*G01W 1/11* (2006.01)
*G01D 11/24* (2006.01)
*G01N 27/407* (2006.01)

(52) U.S. Cl.
CPC ............... *G01W 1/11* (2013.01); *G01D 11/24* (2013.01); *G01N 27/4077* (2013.01); *G01W 1/08* (2013.01)

(58) Field of Classification Search
CPC ...... G01W 1/08; G01W 1/11; G01N 27/4077; G01N 27/121; G01N 22/04; G01D 21/02; G01D 11/24; G01D 11/245
See application file for complete search history.

(56) References Cited

U.S. PATENT DOCUMENTS 2,497,813 A * 2/1950 Darr ..................... B60C 25/142
251/180
5,511,417 A * 4/1996 Paukkunen ............ G01N 25/56
73/29.01
(Continued)

FOREIGN PATENT DOCUMENTS

| JP | 2009-098103 A | 5/2009 |
|---|---|---|
| KR | 100125424 B1 | 7/1997 |
| KR | 10-1045827 B1 | 7/2011 |

OTHER PUBLICATIONS

Korean Intellectual Property Office / ISA, Written Opinion of the International Searching Authority issued on Patent Application No. PCT/KR2015/005084 dated Jul. 21, 2015.

*Primary Examiner* — Randy W Gibson
*Assistant Examiner* — Gedeon M Kidanu
(74) *Attorney, Agent, or Firm* — Perkins IP Law Group LLC; Jefferson Perkins

(57) ABSTRACT

A dual cap for protecting a humidity sensor of a radiosonde of an aerological observation system includes an outer cap and an inner cap. The dual cap surrounds the humidity sensor. The outer cap has an outer ventilation hole formed in its top, and an outer air circulation opening formed in its side periphery. The side periphery of the outer cap also has a first wall that acts as a barrier to air flow. The inner cap is affixed (Continued)

to and is disposed inside of the outer cap. A ceiling of the inner cap faces the outer ventilation hole so as to impose a barrier to air flow. The inner cap further has an inner ventilation hole in its top and an inner air circulation opening formed in its side periphery. The inner air circulation opening faces the first wall of the outer cap.

8 Claims, 6 Drawing Sheets

(56) References Cited

U.S. PATENT DOCUMENTS

| | | | | |
|---|---|---|---|---|
| 5,744,697 | A * | 4/1998 | Martell | G01N 27/4045 |
| | | | | 204/412 |
| 6,673,224 | B2 * | 1/2004 | Shirai | C03C 3/066 |
| | | | | 204/421 |
| 8,016,990 | B2 * | 9/2011 | Taguchi | G01N 27/4077 |
| | | | | 204/428 |
| 8,671,740 | B2 * | 3/2014 | Sekiya | G01N 27/4077 |
| | | | | 204/428 |
| 8,842,024 | B2 | 9/2014 | Lee et al. | |
| 2004/0035700 | A1 * | 2/2004 | Taguchi | G01N 27/4077 |
| | | | | 204/429 |
| 2005/0198810 | A1 * | 9/2005 | Taguchi | G01N 27/4077 |
| | | | | 29/592.1 |
| 2010/0156663 | A1 * | 6/2010 | Pal | G01W 1/08 |
| | | | | 340/870.1 |
| 2011/0126610 | A1 * | 6/2011 | Sekiya | G01N 27/4077 |
| | | | | 73/25.05 |
| 2011/0283774 | A1 * | 11/2011 | Sekiya | G01N 27/4077 |
| | | | | 73/30.01 |
| 2014/0161559 | A1 | 6/2014 | Kim et al. | |

* cited by examiner

[Fig. 1]
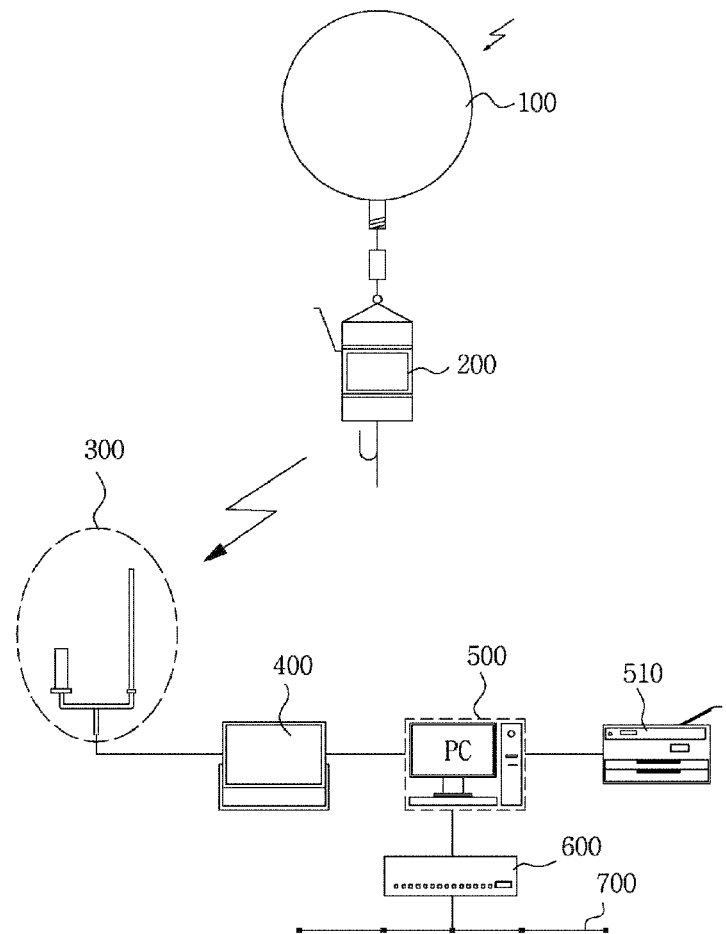

[Fig. 2]
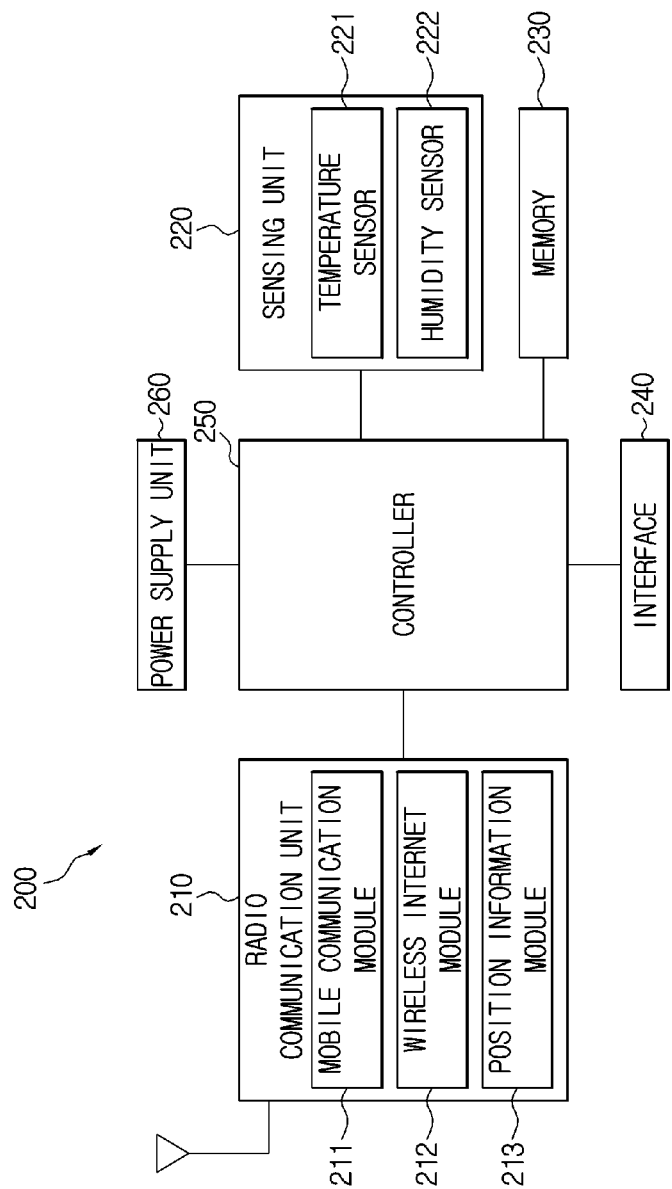

[Fig. 3]
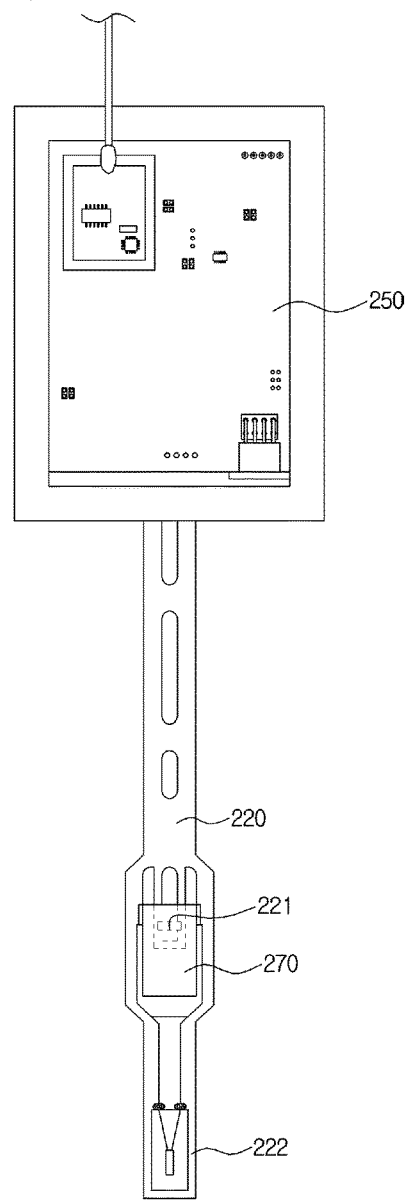
[Fig. 4]
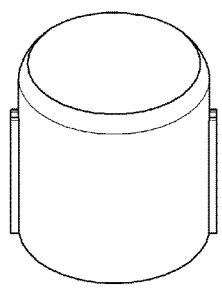

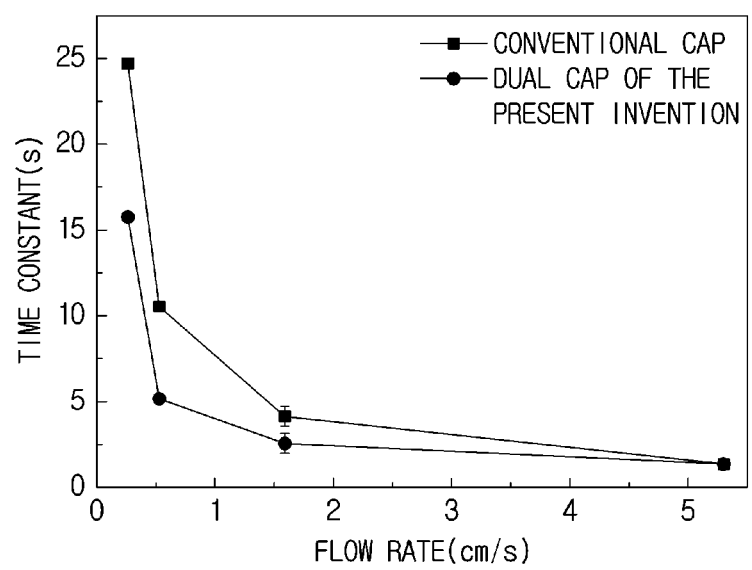
[Fig. 10]

US 10,353,114 B2

DUAL CAP FOR PROTECTING HUMIDITY SENSOR OF RADIOSONDE

TECHNICAL FIELD

The present invention relates to a dual cap for protecting a humidity sensor of a radiosonde, and more particularly, to a dual cap for protecting a humidity sensor of a radiosonde that is configured to have outer cap and an inner cap, thus protecting the humidity sensor from water, and to form air circulation paths therein, thus enhancing the response speed of the humidity sensor.

BACKGROUND ART

The atmosphere surrounding the surface of the earth has a great influence on human life. Among the observation systems used for recognizing the structure and change of the atmosphere, a radiosonde has temperature, humidity and GPS sensors mounted thereon in such a manner as to be carried into the atmosphere by a balloon, thus allowing the upper air state of the atmosphere to be recognized through observation materials transmitted therefrom at given time intervals, Temperature, air pressure and humidity are measured directly by the radiosonde elevated into the air, and wind is measured by calculating the flying distance of the balloon during a given period of time. Generally, there are a LORAN (Long Range Navigation) method and a GPS (Global Positioning System) method for recognizing the position of the radiosonde.

For example, Korean Patent Registration No. 10-1045827 discloses a rising-and-falling type of lower atmosphere observation and testing device, wherein temperature and humidity are observed through various sensors and if the corresponding observation signal and position signal are transmitted to ground, precise observation result values are recognized.

The radiosonde is elevated into the upper air, and as it goes high, it is exposed to rain or passed through cloud, so that the humidity sensor may be wet, thus causing errors in the measurement of humidity.

So as to prevent the humidity sensor from being brought into direct contact with water, the humidity sensor of the conventional radiosonde is covered with a cap.

However, the conventional cap has a structure of surrounding the humidity sensor, so that external air is not rapidly circulated to the humidity sensor located inside the cap, thus making the response speed of the measurement of humidity undesirably decreased.

Accordingly, there is a definite need for the development of a new dual cap capable of preventing the humidity sensor from being brought into direct contact with water and improving the response speed of the measurement of humidity.

DISCLOSURE OF INVENTION

Technical Problem

Accordingly, the present invention has been made in view of the above-mentioned problems occurring in the prior art, and it is an object of the present invention to provide a dual cap for protecting a humidity sensor of a radiosonde to a user.

It is another object of the present invention to provide a dual cap for protecting a humidity sensor of a radiosonde wherein the humidity sensor of the radiosonde is not brought into direct contact with water, thus preventing occurrence of errors in the measurement of humidity.

It is yet another object of the present invention to provide a dual cap for protecting a humidity sensor of a radiosonde wherein external air is circulated well to the interior of the dual cap, thus enhancing the response speed of the humidity sensor.

It is still another object of the present invention to provide a dual cap for protecting a humidity sensor of a radiosonde wherein the dual cap is made by plating the outer surface of an injection molded plastic material, thus being light in weight.

It is yet still another object of the present invention to provide a dual cap for protecting a humidity sensor of a radiosonde wherein the dual cap is made through a 3D printer, thus reducing the manufacturing time thereof.

Solution to Problem

To accomplish the above-mentioned objects, according to a first aspect of the present invention, there is provided a dual cap for protecting a humidity sensor of a sensing unit in a radiosonde of an aerological observation system, the dual cap being disposed so as to surround the humidity sensor, the dual cap including: an outer cap having an outer ventilation hole formed on top thereof, an outer air circulation opening formed on the side periphery thereof to pass air therethrough, and a first wall formed on the side periphery thereof to close the flow of air; and an inner cap located inside the outer cap in such a manner as to be fixed to the outer cap and having an inner air circulation opening formed on the side periphery thereof to pass air therethrough, the inner air circulation opening facing the first wall of the outer cap.

According to the present invention, preferably, the outer cap further includes fixing grooves formed on both sides thereof in such a manner as to fix the outer cap to the sensing unit.

According to the present invention, preferably, the inner cap is directly connected and fixed to the sensing unit.

According to the present invention, preferably, the outer cap further includes a rib adapted to connect at least a portion of the inner periphery of the outer cap with at least a portion of the outer periphery of the inner cap so as to fix the inner cap to the outer cap.

According to the present invention, preferably, the rib is provided plurally.

According to the present invention, preferably, the outer ventilation hole, the outer air circulation opening, and the inner air circulation opening are formed plurally.

According to the present invention, preferably, the outer cap and the inner cap are made by plating an injection-molded plastic material.

According to the present invention, preferably, the outer cap and the inner cap are made by means of a 3D printer.

According to the present invention, preferably, the humidity sensor is a polymer thin film sensor using a polymer thin film capacitor.

According to the present invention, preferably, the inner cap includes an inner ventilation hole and a first ceiling formed on top thereof, the inner ventilation hole being formed to pass air therethrough and the first ceiling formed to close the flow of air thereby.

According to the present invention, preferably, the first ceiling is located to face the outer ventilation hole of the outer cap.

To accomplish the above-mentioned objects, according to a second aspect of the present invention, there is provided a method for increasing ventilation using a dual cap, the method including the steps of: allowing external air from an outer cap to flow to the interior of the outer cap through a first ventilation hole and a first air circulation door; allowing the air flowing to the interior of the outer cap to flow to the interior of the inner cap through the second air circulation door formed on the inner cap; blocking the introduction of water from the outside of the outer cap through the closed portion of the outer cap; and if water enters the outer cap, blocking the introduction of water through the closed portion of the inner cap.

To accomplish the above-mentioned objects, according to a third aspect of the present invention, there is provided a recording medium having program types of commands executable by a digital processing unit in such a manner as to be readable by the digital processing unit to carry out a method for increasing ventilation using a dual cap, wherein the method includes the steps of: allowing external air from an outer cap to flow to the interior of the outer cap through a first ventilation hole and a first air circulation door; allowing the air flowing to the interior of the outer cap to flow to the interior of an inner cap through a second air circulation door formed on the inner cap; blocking the introduction of water from the outside of the outer cap through the closed portion of the outer cap; and if water enters the outer cap, blocking the introduction of water through the closed portion of the inner cap.

Advantageous Effects of Invention

According to the present invention, the dual cap can be provided to a user, while protecting the humidity sensor of the radiosonde from water.

In more detail, the humidity sensor of the radiosonde is not brought into direct contact with water, thus preventing occurrence of errors in the measurement of humidity.

Further, external air is circulated well to the interior of the dual cap, thus enhancing the response speed of the humidity sensor.

Furthermore, the light dual cap is provided to the user since it is made by means of injection molding of a plastic material and plating of the outer surface thereof.

Besides, the dual cap is made through a 3D printer, thus reducing the manufacturing time.

BRIEF DESCRIPTION OF DRAWINGS

FIG. 1 is a schematic view showing a general aerological observation system.

FIG. 2 is a block diagram showing a radiosonde applied to the present invention.

FIG. 3 is a plan view showing the radiosonde applied to the present invention.

FIG. 4 is a perspective view showing a conventional cap for protecting a humidity sensor of the radiosonde.

FIG. 10 is a graph showing the test results of flow rate to time constant measured by the conventional cap and the dual cap according to the present invention.

MODE FOR THE INVENTION

Figure 5:
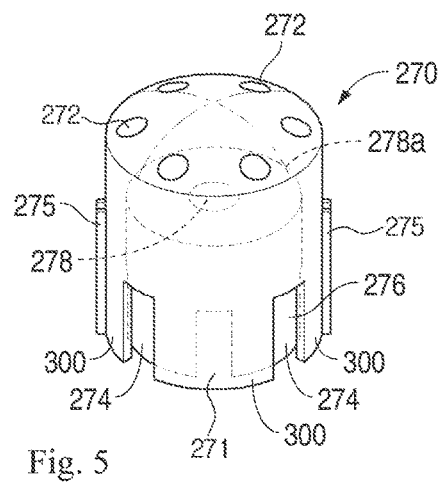
FIG. 5 is a perspective view showing a dual cap for protecting a humidity sensor of a radiosonde according to the present invention.

A radiosonde is an instrument used for an aerological observation system so as to monitor the upper air below about 80 km above the surface of ground. The aerological observation system plays an important role in the association with the weather above ground. Referring to FIG. 1, the aerological observation system will be explained.

FIG. 1 is a schematic view showing a general aerological observation system.

As shown in FIG. 1, the aerological observation system includes a balloon 100, a radiosonde 200, a UHF antenna 300, radio signal demodulation means 400, a PC 500, a printer 510, a hub 600, and an intranet 700.

In this case, the balloon 100 is filled with helium or the like to carry the radiosonde 200 to a weather observation position.

The radiosonde 200 is connected to the balloon 100 to observe the weather condition in the atmosphere. Further, the radiosonde 200 modulates the observed weather condition information together with position information by means of frequency hopping spread spectrum (FHSS) and transmits the modulated information by radio to the ground.

The UHF antenna 300 receives the weather condition information and the position information modulated by means of the frequency hopping spread spectrum from the radiosonde 200. At this time, the UHF antenna 300 may be formed of a pair of directional and omnidirectional antennas.

The radio signal demodulation means 400 demodulates the weather condition information and the position information modulated by means of the frequency hopping spread spectrum from the UHF antenna 300 into digital data and transmits the demodulated digital data to the PC 500 analyzing the weather condition information data.

The PC 500 stores and analyzes the aerological observation data transmitted from the radiosonde 200 and transforms the data into the form of materials necessary for weather stations. The transformed materials are outputted through the printer 510, displayed on a monitor, or transmitted to the weather stations through the hub 600 and the intranet 700.

Next, the radiosonde 200 used for the aerological observation system will be explained with reference to FIG. 2.

FIG. 2 is a block diagram showing the radiosonde applied to the present invention.

The radiosonde 200 includes a radio communication unit 210, a sensing unit 220, a memory 230, an interface 240, a controller 250 and a power supply unit 260. The components as shown in FIG. 2 are not necessarily provided for the radiosonde 200, and therefore, a larger or smaller number of components may be provided for the radiosonde 200.

Now, the components of the radiosonde 200 will be described in the order mentioned above.

The radio communication unit 210 includes one or more modules capable of performing radio communication between the radiosonde 200 and a radio communication system or between the radiosonde 200 and the network on which the radiosonde 200 is located. For example, the radio communication unit 210 serves to transmit the data outputted from the controller 250 to the UHF antenna located on the ground.

On the other hand, the radio communication unit 210 includes a mobile communication module 211, a wireless internet module 212, and a position information module 213.

The mobile communication module 211 transmits and receives radio signals to and from at least one of a base station, an external terminal, and a server on a mobile communication network.

The wireless internet module 212 serves to connect wireless internet thereto and is internally or externally embedded in the radiosonde 200. The wireless internet module 212 has wireless internet technologies, such as WLAN (Wireless LAN, which is Wi-Fi), Wibro (Wireless broadband), Wimax (World Interoperability for Microwave Access), HSDPA (High Speed Downlink Packet Access), and the like.

The position information module 213 serves to recognize the position of the radiosonde 200, and there is a GPS (Global Position System) module as a representative example of the position information module 213. According to the current technology, the position information module 213 calculates the information of distance and time from three or more satellites, applies a triangulation method to the calculated information, and accurately obtains three dimensional current position information according to latitude, longitude, and altitude. At present, generally, the position and time information is calculated from three satellites, and errors on the calculated position and time information are corrected by using another satellite. Further, the position information module 213 calculates the current position in real time, thus calculating speed information.

The position information module 213 serves as a navigation system that receives a GPS signal from an antenna ANT so as to obtain the current position material of the radiosonde 200 in the upper atmosphere. Of course, the position information module 213 may receive a LORAN (Long Range Navigation)-C signal, not GPS signal.

The sensing unit 220 senses the current states of the radiosonde 200, such as, opening and closing state, position, direction and acceleration/deceleration of the radiosonde 200 and generates the sensing signals controlling the operations of the radiosonde 200. Further, the sensing unit 220 serves to sense whether power supply is conducted by the power supply unit 260 and whether the interface 240 is coupled to external devices.

On the other hand, the sensing unit 220 includes a temperature sensor 221 and a humidity sensor 222.

The temperature sensor 221 senses a temperature in the upper atmosphere, and the humidity sensor 222 senses humidity in the upper atmosphere.

On the other hand, the humidity sensor 222 is formed of a polymer thin film humidity sensor. The polymer thin film humidity sensor measures capacitance through a polymer thin film capacitor. If water in the air is permeated into a polymer thin film, capacitance is increased, and contrarily, if humidity is low, capacitance is decreased. Accordingly, the polymer thin film humidity sensor measures the humidity through the polymer thin film capacitor.

In addition to the temperature sensor 221 and the humidity sensor 222, the sensing unit 220 further includes other sensors like an atmospheric pressure sensor.

The memory 230 stores programs for the process and control of the controller 250 and temporarily stores the data inputted and outputted thereinto/therefrom. Further, the memory 230 also stores the usage frequency of the data therein.

The memory 230 includes at least one selected from the group consisting of flash memory, hard disk, multimedia card micro, card type memory (for example, SD or XD memory), RAM (Random Access Memory), SRAM (Static Random Access Memory), ROM (Read-Only Memory), EEPROM (Electrically Erasable Programmable Read-Only Memory), PROM (Programmable Read-Only Memory), magnetic memory, magnetic disk, and optical disk. The radiosonde 200 may be operated with the web storage performing the storing function of the memory 230 on internet.

The interface 240 serves as a path to all external devices connected to the radiosonde 200. The interface 240 receives data from the external devices or power from the outside, transmits the received data to the components of the radiosonde 200, and transmits the data of the radiosonde 200 to the external devices.

For example, the interface 240 includes ports connecting devices having an exterior charger port, a wire/wireless data port, a memory card port, and an identification module.

The identification module is a chip that stores various information for authenticating the use right of the radiosonde 200 and includes a user identify module UIM, a subscriber identify module SIM, a universal subscriber identify module USIM, and the like.

The controller 250 controls the whole operation of the radiosonde 200 and outputs the weather information sensed by the sensing unit 220 and the position information received by the position information module 213, as digital data. At this time, the digital data outputted from the controller 250 is transmitted to a radiosonde transmitter.

The power supply unit 260 receives external and internal power by the control of the controller 250 and supplies the power necessary for the components of the radiosonde 200 to the components.

The various embodiments described herein can be carried out in a recording media readable through a computer or a device similar to the computer with software, hardware, or the combination of them.

According to the hardware implementation, first, the embodiments described herein may be carried out by using at least one selected from the group consisting of ASICs (Application Specific Integrated Circuits), DSPs (Digital Signal Processors), DSPDs (Digital Signal Processing Devices), PLDs (Programmable Logic Devices), FPGAs (Field Programmable Gate Arrays), processors, controllers, micro-controllers, microprocessors, and electrical units conducting other functions. In some cases, the embodiments described herein may be carried out by the controller 250 itself.

According to the software implementation, next, the embodiments like procedures and functions described herein may be carried out with separate software modules. Each software module can conduct one or more functions and operations explained in the present invention. Software codes can be implemented by software applications having appropriate program languages. The software codes are stored in the memory 230 and executed by the controller 250.

Now, an explanation on the outer appearance of the radiosonde 200 will be given with reference to FIG. 3.

FIG. 3 is a plan view showing the radiosonde applied to the present invention.

As shown in FIG. 3, the radiosonde 200 includes the sensing unit 220, the controller 250, the radio communication unit 210, and a cap 270.

As mentioned above, the sensing unit 220 includes the temperature sensor 221 and the humidity sensor 222 to measure temperature and humidity. Further, the controller 250 controls the whole operation of the radiosonde 200, and the radio communication unit 210 serves to transmit the data under the control of the controller 250.

The cap 270 serves to protect the humidity sensor 222. The radiosonde 200 is suspended to the upper air, and as it goes high, the radiosonde 200 is exposed to rain or passed through cloud, so that the humidity sensor 222 may be brought into direct contact with water. So as to prevent the humidity sensor 222 from being wet, as shown in FIG. 3, the humidity sensor 222 of the sensing unit 220 is covered with the cap 270.

FIG. 4 is a perspective view showing a conventional cap for protecting a humidity sensor of the radiosonde. The conventional cap has a structure of surrounding the humidity sensor 222, so that external air is not rapidly circulated to the humidity sensor 222 located inside the cap, thus making the response speed of humidity measurement undesirably decreased.

So as to solve the above problems suffered in the conventional cap, a dual cap 270 according to the present invention is suggested to prevent the humidity sensor 222 from being brought into direct contact with water and to improve the response speed of the measurement of humidity.

Referring to FIGS. 5 to 8, the dual cap 270 according to a preferred embodiment of the present invention will be explained. On the other hand, a preferred embodiment of the present invention as will be described is not intended to limit the invention to the claims appended hereto, and it is to be understood that the disclosed embodiment is merely exemplary of the invention, which can be embodied in various forms.

Figure 6:
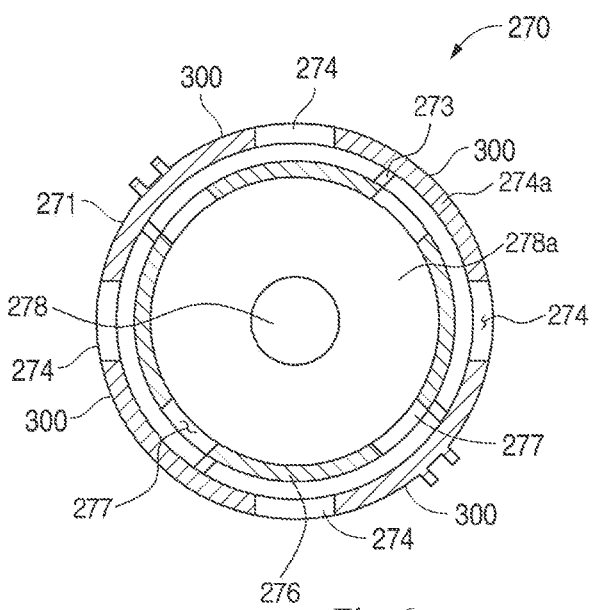
FIG. 6 is a plan view showing the dual cap according to the present invention.
Figure 7:
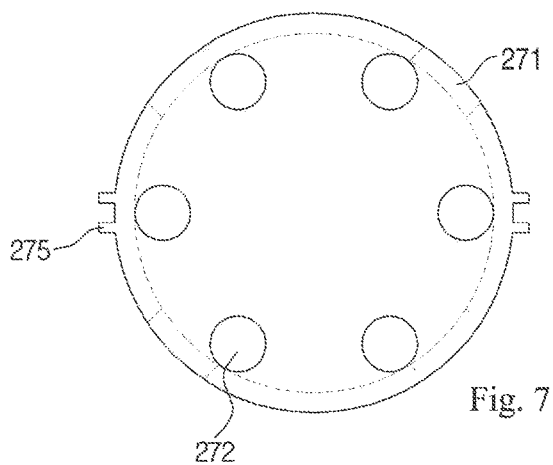
FIG. 7 is a bottom view showing the dual cap according to the present invention.
Figure 8:
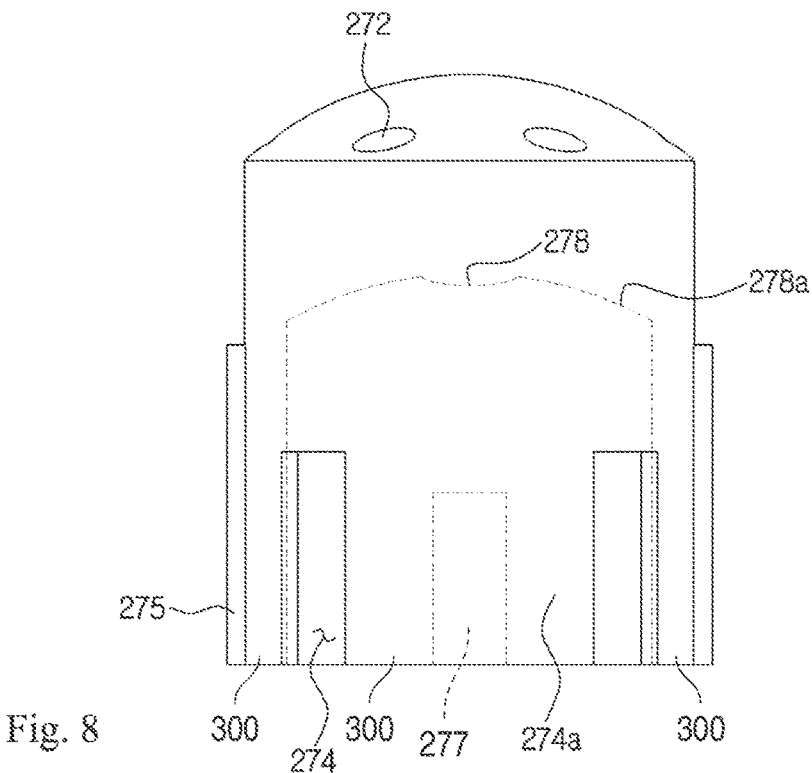
FIG. 8 is a side view showing the dual cap according to the present invention.

FIG. 5 is a perspective view showing a dual cap 270 for protecting a humidity sensor of a radiosonde according to the present invention. Further, FIG. 6 is a plan view showing the dual cap according to the present invention, FIG. 7 is a bottom view showing the dual cap according to the present invention, and FIG. 8 is a side view showing the dual cap according to the present invention.

As shown in FIGS. 5 to 8, the dual cap 270 includes an outer cap 271 and an inner cap 276. Further, the outer cap 271 includes outer ventilation holes 272, ribs 273, outer air circulation openings 274, and fixing grooves 275, and the inner cap 276 includes inner air circulation openings 277 and an inner ventilation hole 278. First walls 300 of the outer cap 271 respectively extend between pairs of the outer air circulation openings 274.

The outer cap 271 is fixed to the humidity sensor 222 so as to primarily prevent the humidity sensor 222 from being brought into direct contact with water. The outer cap 271 is made by means of injection molding of a plastic material and plating of the outer surface thereof.

Further, the outer cap 271 may be formed unitarily with the inner cap 276 by means of a 3D printer. The 3D printer is a machine making a three-dimensional object on the basis of a 3D drawing, and in this case, the three-dimensional object is generally made of a plastic material. In addition to the plastic, of course, wax, paper, rubber and the like may be used.

The outer ventilation holes 272 are formed on top of the outer cap 271 in such a manner as to circulate external air from the outer cap 271 to the interior of the outer cap 271 and thus to improve the response speed of the humidity sensor 222. The number of outer ventilation holes 272 is six, but if necessary, it may be freely changed.

Next, the ribs 273 connect the inner cap 276 and the outer cap 271 with each other. The ribs 273 connect the outer periphery of the inner cap 276 and the inner periphery of the outer cap 271 to fix the inner cap 276 and the outer cap 271 to each other. Further, the upper outer periphery of the inner cap 276 may be connected to the upper inner periphery of the outer cap 271. In addition to the ribs 273, that is, various methods may be adopted to connect the inner cap 276 and the outer cap 271 with each other.

Next, the outer air circulation openings 274 are formed along the side periphery of the outer cap 271 in such a manner as to circulate external air to the interior of the outer cap 271 and thus to improve the response speed of the humidity sensor 222. The number of outer air circulation openings 274 is four as illustrated in the drawings, but it may be freely changed if necessary.

Next, the fixing grooves 275 serve to fix the outer cap 271 to the sensing unit 220, and as shown in FIG. 3, it is fitted to a position of the sensing unit 220 where the humidity sensor 222 is disposed to fix the outer cap 271 to the sensing unit 220. In addition to the fixing grooves 275, however, the outer cap 271 may be fixed to the humidity sensor 222 by means of soldering or tape.

On the other hand, the inner cap 276 is fixed to the outer cap 271 through the ribs 273 or fixed directly to the sensing unit 220 so as to primarily prevent the humidity sensor 222 from being brought into direct contact with water. The inner cap 276 includes the inner air circulation openings 277 and the inner ventilation hole 278. The inner cap 276 is made by means of injection molding of a plastic material and plating of the outer surface thereof. In the same manner as the outer cap 271, further, the inner cap 276 may be formed unitarily with the outer cap 271 by means of a 3D printer. The 3D printer is a machine making a three-dimensional object on the basis of a 3D drawing, and in this case, the three-dimensional object is generally made of a plastic material. In addition to the plastic, of course, wax, paper, rubber and the like may be used.

The inner air circulation openings 277 are formed along the side periphery of the inner cap 276 in such a manner as to circulate external air to the interior of the inner cap 276 and thus to improve the response speed of the humidity sensor 222.

If the inner air circulation openings 277 and the outer air circulation openings 274 are formed on the same position as each other, they would not protect from the water intruding from the outside, and accordingly, the inner air circulation openings 277 and the outer air circulation openings 274 are desirably formed in an alternating manner. The inner air circulation openings 277 face respective first walls 300 of the outer cap 271.

Like the outer circulation ventilation holes 272, further, the inner circulation ventilation hole 278 is formed on top of the inner cap 276, i.e., on first ceiling 278a, to improve the ventilation of the inner cap 276. Even if not shown, a plurality of inner circulation holes may be formed, like the outer circulation ventilation holes 272 of the outer cap 271, and in this case, the inner circulation ventilation holes desirably do not face the outer circulation ventilation holes 272 so as to prevent water from entering the humidity sensor 222.

Hereinafter, the response speeds of the humidity sensors will be compared with each other through the test results using the conventional cap and the dual cap according to the present invention.

Figure 9:
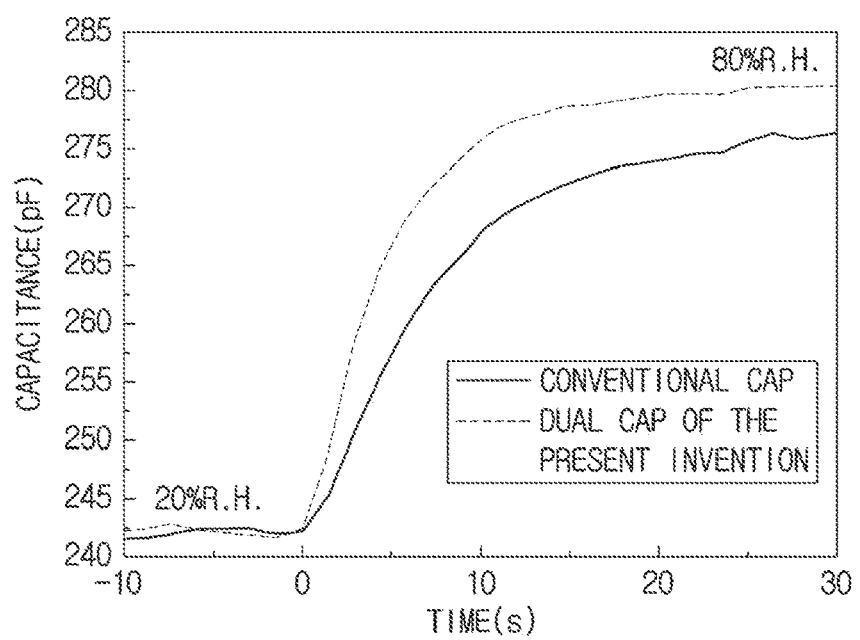
FIG. 9 is a graph showing the capacitances measured by the conventional cap and the dual cap according to the present invention.

FIG. 9 is a graph showing the capacitances measured by the conventional cap and the dual cap according to the present invention.

As shown in FIG. 9, the test is conducted under a temperature of 25° C. and a flow rate of 0.1 SLM (Standard Liter per Minute).

As shown, if humidity is raised from 20% R.H. (Relative Humidity) to 80% R.H., the increasing speed and value of the capacitance when the dual cap of the present invention is used are higher than those of the capacitance when the conventional cap is used.

The higher the capacitance measured by the humidity sensor is, the higher the humidity measured is. It can be therefore appreciated that the response speed of the humidity sensor when the dual cap of the present invention is used is higher than that when the conventional cap is used.

FIG. 10 is a graph showing the test results of flow rate to time constant measured by the conventional cap and the dual cap according to the present invention.

As shown in FIG. 10, the time constants when the dual cap of the present invention is used are lower than those when the conventional cap is used. This means that the sensing speed of the humidity sensor when the dual cap of the present invention is used is higher than that when the conventional cap is used.

As described above, the dual cap protecting the humidity sensor of the radiosonde according to the present invention are not limited to the above-mentioned configuration and method, but may be freely varied through the combination of the whole or a portion thereof.

After that, the dual cap according to the present invention can be provided to a user, while protecting the humidity sensor of the radiosonde from water.

In more detail, the humidity sensor used for the radiosonde is not brought into direct contact with water, thus preventing occurrence of errors in the measurement of humidity.

Further, external air is circulated well to the interior of the dual cap, thus enhancing the response speed of the humidity sensor.

Furthermore, the light dual cap is provided to the user since it is made by means of injection molding of a plastic material and plating of the outer surface thereof.

Besides, the dual cap is made through a 3D printer, thus reducing the manufacturing time thereof.

While the present invention has been described with reference to the particular illustrative embodiments, it is not to be restricted by the embodiment but only by the appended claims. It is to be appreciated that those skilled in the art can change or modify the embodiments without departing from the scope and spirit of the present invention.

The invention claimed is:

1. A dual cap disposed so as to surround a humidity sensor of a sensing unit in a radiosonde of an aerological observation system, the dual cap comprising:

an outer cap having at least one outer ventilation hole formed on top thereof, at least one outer air circulation opening formed on a side periphery of the outer cap to pass air therethrough, and a first wall formed on the side periphery of the outer cap to close the flow of air; and an inner cap located inside the outer cap in such a manner as to be fixed to the outer cap, the inner cap having a side periphery, an inner air circulation opening formed on the side periphery of the inner cap to pass air therethrough, the inner air circulation opening facing the first wall of the outer cap, the side periphery of the inner cap having an outer surface, the side periphery of the outer cap having an inner surface and an outer surface opposed to the inner surface, a plurality of spaced-apart ribs spacing the outer surface of the side periphery of the inner cap from the inner surface of the side periphery of the outer cap, a first pair of elongate fixing groove ribs radially outwardly extending from the outer surface of the side periphery of the outer cap at a first location and defining therebetween a first fixing groove, a second pair of elongate fixing groove ribs radially outwardly extending from the outer surface of the side periphery of the outer cap at a second location opposite the first location and defining therebetween a second fixing groove, the first and second fixing grooves fixing the outer cap to the sensing unit;

a top of the inner cap having a first ceiling facing the outer ventilation hole for closing the flow of air, an inner ventilation hole of the top of the inner cap displaced from the first ceiling and formed to pass air therethrough.

2. The dual cap according to claim 1, wherein the inner cap is directly connected and fixed to the sensing unit.

3. The dual cap according to claim 1, wherein the outer ventilation hole, the outer air circulation opening, and the inner air circulation opening are formed plurally.

4. The dual cap according to claim 1, wherein the outer cap and the inner cap are made by plating an injection-molded plastic material.

5. The dual cap according to claim 1, wherein the outer cap and the inner cap are made by means of a 3D printer.

6. The dual cap according to claim 1, wherein the humidity sensor is a polymer thin film sensor using a polymer thin film capacitor.

7. A radiosonde comprising a dual cap according to claim 1.

8. An aerological observation system comprising a dual cap according to claim 1.

* * * * *